(12) United States Patent
Pradel et al.

(10) Patent No.: US 9,636,644 B2
(45) Date of Patent: May 2, 2017

(54) AERATION DEVICE FOR BIOREACTORS

(75) Inventors: Guenter Pradel, Goettingen (DE); Stefan Weisshaar, Adelebsen (DE); Gerhard Greller, Goettingen (DE); Ute Husemann, Goettingen (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 251 days.

(21) Appl. No.: 13/508,074

(22) PCT Filed: Oct. 28, 2010

(86) PCT No.: PCT/EP2010/006601
§ 371 (c)(1),
(2), (4) Date: May 4, 2012

(87) PCT Pub. No.: WO2011/057718
PCT Pub. Date: May 19, 2011

(65) Prior Publication Data
US 2012/0313267 A1    Dec. 13, 2012

(30) Foreign Application Priority Data

Nov. 12, 2009  (DE) .................. 10 2009 052 670

(51) Int. Cl.
*B01F 3/04* (2006.01)
*C12M 1/00* (2006.01)

(52) U.S. Cl.
CPC ...... *B01F 3/04531* (2013.01); *B01F 3/04262* (2013.01); *C12M 29/06* (2013.01); *B01F 3/04099* (2013.01); *B01F 3/04106* (2013.01); *B01F 2003/04673* (2013.01)

(58) Field of Classification Search
CPC ........ B01F 2003/04148; B01F 3/04106; B01F 3/04262; B01F 2003/04326; B01F 3/04248; B01F 2003/04283; B01F 2003/04354; B01F 2003/04361; B01F 2003/04368; B01F 2003/0439; B01F 2003/04297; B01F 3/04531; B01F 2003/04673; B01F 3/04099; C12M 29/06
USPC ....................................... 261/124
See application file for complete search history.

(56) References Cited

U.S. PATENT DOCUMENTS 3,953,554 A * 4/1976 Loughridge .................. 261/124
4,165,286 A * 8/1979 Schreiber ............ B01F 3/04269
                                                    210/220
4,207,275 A * 6/1980 Stanton, Jr. ......... B01F 3/04262
                                                    210/221.2
4,521,349 A * 6/1985 Weber ................. B01F 3/04262
                                                    209/169

(Continued)

FOREIGN PATENT DOCUMENTS

BE  WO 2007134267 A2 * 11/2007 .......... B01F 3/04269
DE           813 995          9/1951
(Continued)

*Primary Examiner* — Amber R Orlando
*Assistant Examiner* — Stephen Hobson
(74) *Attorney, Agent, or Firm* — Gerald E. Hespos; Michael J. Porco; Matthew T. Hespos

(57) ABSTRACT

Aeration device for bioreactors with a first aeration element with gas outlet openings of a first size and with at least one second aeration element with gas outlet openings of a second size, the aeration elements being formed by a common housing with separate aeration channels.

15 Claims, 6 Drawing Sheets

(56) References Cited

U.S. PATENT DOCUMENTS

| | | | |
|---|---|---|---|
| 4,557,879 A | 12/1985 | Weber | |
| 4,769,221 A * | 9/1988 | Marihart | B01F 3/088 261/124 |
| 4,888,294 A * | 12/1989 | Van Wezel | C12M 27/02 435/290.1 |
| 5,166,072 A * | 11/1992 | Krauling | C02F 3/085 210/151 |
| 5,198,362 A | 3/1993 | Forsyth et al. | |
| 5,241,992 A | 9/1993 | Oehlbeck et al. | |
| 5,314,644 A * | 5/1994 | Michelsen | B01F 7/005 209/170 |
| 5,422,043 A * | 6/1995 | Burris | A61L 2/202 261/122.1 |
| 5,622,857 A * | 4/1997 | Goffe | B01L 7/02 210/321.8 |
| 5,753,014 A * | 5/1998 | Van Rijn | B01D 39/1692 55/524 |
| 5,798,254 A | 8/1998 | Cheng | |
| 5,858,283 A * | 1/1999 | Burris | B01F 3/04269 156/290 |
| 8,172,206 B2 * | 5/2012 | St. Lawrence | B01F 3/04609 210/219 |
| 8,568,657 B2 * | 10/2013 | Braet | B01F 3/04262 422/26 |
| 8,833,743 B2 * | 9/2014 | Ko | B01F 3/04262 261/121.1 |
| 2005/0077239 A1 * | 4/2005 | Frisch | C02F 3/085 210/616 |
| 2005/0151281 A1 * | 7/2005 | Tharp | B01F 3/04269 261/122.1 |
| 2005/0272146 A1 * | 12/2005 | Hodge | B01F 13/0827 435/289.1 |
| 2006/0033222 A1 * | 2/2006 | Godfrey | B01F 3/04262 261/122.1 |
| 2007/0126135 A1 * | 6/2007 | Abello | B01F 3/04269 261/122.1 |
| 2007/0238176 A1 * | 10/2007 | MacDonald | B01D 63/02 435/395 |
| 2008/0068920 A1 * | 3/2008 | Galliher | B01F 3/04106 366/102 |
| 2009/0035856 A1 * | 2/2009 | Galliher | C12M 23/14 435/383 |
| 2009/0129201 A1 * | 5/2009 | Terentiev | B01F 1/0011 366/273 |
| 2009/0130757 A1 * | 5/2009 | Terentiev | 435/394 |
| 2010/0174099 A1 * | 7/2010 | Behkish | B01J 8/006 549/518 |
| 2010/0255526 A1 * | 10/2010 | Braet | B01F 3/04262 435/29 |
| 2011/0013473 A1 * | 1/2011 | Ludwig | B01F 3/04269 366/101 |
| 2011/0038222 A1 * | 2/2011 | Ludwig et al. | 366/102 |
| 2011/0313062 A1 * | 12/2011 | Ruppel | B01J 8/1818 518/700 |
| 2012/0129257 A1 * | 5/2012 | Yu | C12M 23/44 435/395 |
| 2013/0082410 A1 * | 4/2013 | Goodwin | B01F 15/0085 261/42 |
| 2015/0001744 A1 * | 1/2015 | Mollen | B01F 3/04269 261/122.1 |
| 2015/0246835 A1 * | 9/2015 | Ko | C02F 3/201 210/151 |
| 2016/0244710 A1 * | 8/2016 | Wood | B01F 7/22 |

FOREIGN PATENT DOCUMENTS

| | | | | |
|---|---|---|---|---|
| DE | 975 813 | | 12/1962 | |
| DE | 3317917 A1 | * | 11/1984 | B01F 3/04262 |
| DE | 3434669 A1 | * | 4/1986 | A01C 3/026 |
| DE | 36 21 328 | | 1/1988 | |
| DE | 3632772 C1 | * | 4/1988 | B01F 3/04262 |
| DE | 689 09 667 | | 2/1994 | |
| DE | EP 0704237 A2 | * | 4/1996 | B01F 3/0412 |
| DE | 199 53 137 | | 5/2001 | |
| DE | 697 09 276 | | 8/2002 | |
| DE | WO 2008077430 A1 | * | 7/2008 | B01D 53/1481 |
| DE | WO 2014041146 A1 | * | 3/2014 | A01K 63/042 |
| EP | 0761298 A2 | * | 3/1997 | B01F 5/046 |
| EP | 1 884 561 | | 2/2008 | |
| FR | WO 2009116002 A1 | * | 9/2009 | B01F 3/04269 |
| FR | WO 2009115926 A3 | * | 11/2009 | B01F 3/04269 |
| GB | 765623 A | * | 1/1957 | B01F 3/04113 |
| GB | 1478223 A | * | 6/1977 | B01F 3/04262 |
| JP | WO 2010113335 A1 | * | 10/2010 | B01D 53/1425 |
| NO | CA 2460354 A1 | * | 3/2003 | A01K 63/042 |
| RU | 2334686 C2 | * | 9/2008 | |
| UA | EP 2463243 A1 | * | 6/2012 | B01F 3/04269 |
| WO | 2008/088371 | | 7/2008 | |
| WO | 2009/115926 | | 9/2009 | |
| WO | 2009/116002 | | 9/2009 | |
| WO | WO 2009116002 A1 | * | 9/2009 | B01F 3/04 |
| WO | 2009/122310 | | 10/2009 | |
| WO | WO 2015142881 A1 | * | 9/2015 | B01F 3/04248 |

\* cited by examiner

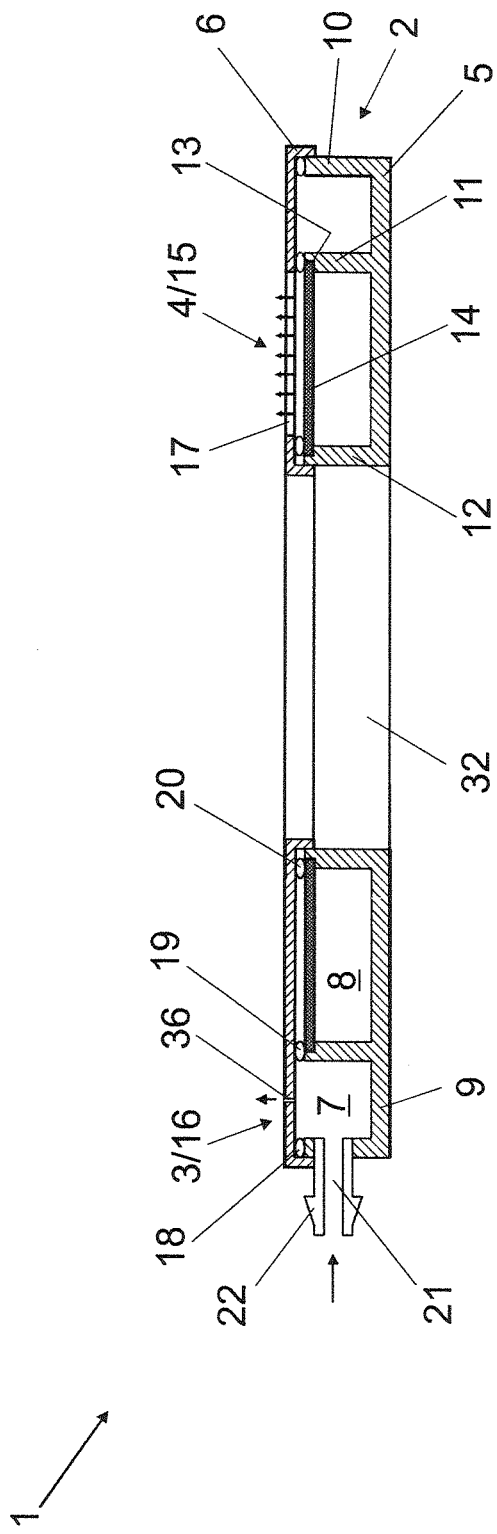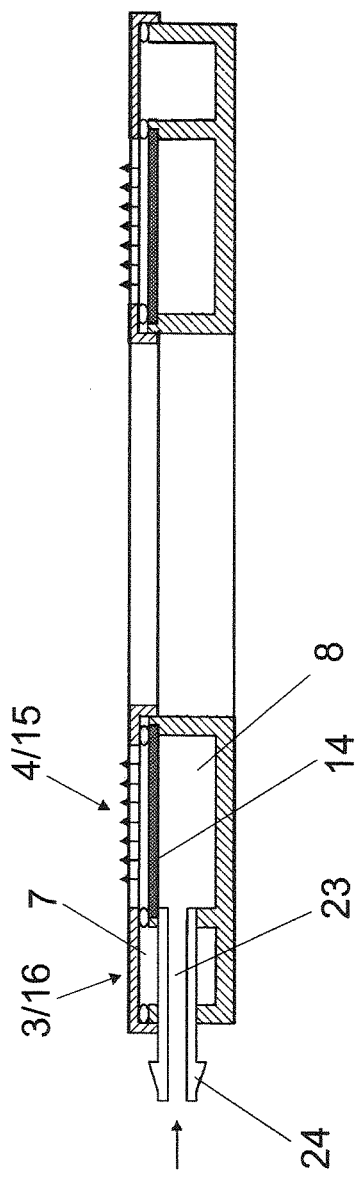

AERATION DEVICE FOR BIOREACTORS

BACKGROUND OF THE INVENTION

1. Field of the Invention

The invention relates to an aeration device for bioreactors with a first aeration element with gas outlet openings of a first size and with at least one second aeration element with gas outlet openings of a second size.

2. Description of the Related Art

Provision of an oxygen supply is a key factor in cellular metabolic processes. Although animal cell cultures consume substantially less oxygen than bacteria and yeast cultures, ensuring an efficient supply is the greatest challenge facing the operation of a cell culture bioreactor. In addition to supplying the cells with oxygen, the concentration of dissolved carbon dioxide also plays a part as a controlled variable.

There are two conventional aeration methods: aerating the headspace of the bioreactor and direct injection of the gases through aeration rings. For this purpose, use is made not only of the aeration rings known from fermenters with bores or gas outlet openings of for example 0.8 mm but also of "microspargers" made from sintered plastics with pore sizes of for example 20 to 45 µm, which likewise form gas outlet openings. Both kinds have specific advantages and drawbacks. The aeration ring produces larger bubbles, which means that higher gas throughput rates are required to achieve the same "oxygen transfer rate". With its relatively large bubbles, the ring sparger is suitable for stripping or sweeping out CO2 with air, for example. With its relatively small bubbles, the microsparger is particularly suitable for supplying oxygen. One drawback, however, is that under unfavorable conditions foaming may occur due to the relatively smaller bubbles.

Aeration devices are used as part of automated bioreactor aeration systems, for example single-use reactors, the supply of air, oxygen, carbon dioxide and nitrogen being mutually independently controllable. Sensors for oxygen partial pressure and pH facilitate the control of these important process parameters.

WO 2009/122310 A2, WO 2009/115926 A2 and WO 2009/116002 A1 disclose a single-use bioreactor with a mixer and with an aeration device arranged on the bottom of the reactor interior. It is known here to arrange two aeration elements on the bottom which take the form of opposing, mating ring segments.

Drawbacks of this aeration device, which has in principle proved effective, are that, on the one hand, it must be fastened in relatively complex manner to the bottom of the reactor and that, on the other hand, it is difficult to arrange a plurality of such aeration elements optimally relative to the stirrer or mixer.

An aeration device for bioreactors is furthermore known from WO 2008/088371 A2, in which for example two aeration elements with different gas outlet openings may be fastened to the bottom of the reactor.

One drawback here is that the aeration elements are fastened in relatively complex manner to the bottom of the reactor. A further drawback is that the individual aeration element is here not optimally arranged relative to the mixer.

The object of the present invention is accordingly to improve the known aeration devices for bioreactors in such a manner that, on the one hand, they are simpler to fasten and, on the other hand, each aeration element is optimally positioned relative to a mixing element arranged in the reactor interior.

SUMMARY OF THE INVENTION

This object is achieved in conjunction with an aeration device for bioreactors with a first aeration element with gas outlet openings of a first size and with at least one second aeration element with gas outlet opening of a second size in that the aeration elements are formed by a common housing with separate aeration channels.

Thanks to the common housing, the aeration device may be arranged simply and centrally relative to a mixer while occupying little space.

According to a preferred embodiment of the invention, the housing takes the form of an annular disk in which the at least two aeration elements are arranged concentrically to one another. The concentric arrangement of the aeration elements enables an optimum arrangement relative to a mixer or stirrer.

According to a preferred embodiment of the invention, the first aeration element takes the form of a ring sparger with gas outlet openings of greater than 0.1 mm in diameter, while the second aeration element takes the form of a microsparger with gas outlet openings of less than 0.1 mm in diameter. The gas outlet openings of the microsparger are here formed of a porous material, for example a sintered plastics material. In this manner, both a ring sparger and a microsparger are compactly arranged in a common housing in a small space.

According to a further preferred embodiment of the invention, the first aeration element and the second aeration element take the form of a ring sparger with in each case two differently sized gas outlet openings, the gas outlet openings being larger than 0.1 mm.

According to a further preferred embodiment of the invention, the first aeration element and the second aeration element take the form of a microsparger with in each case two differently sized gas outlet openings, the gas outlet openings being smaller than 0.1 mm.

According to another preferred embodiment of the invention, the housing comprises a lower part, in which are arranged the aeration channels with in each case a radially extending inflow. In this manner, each of the separately arranged aeration channels comprises a dedicated radially extending inflow.

According to a further preferred embodiment of the invention, the lower part is covered by an upper part which covers the aeration channel of the ring sparger and comprises the gas outlet openings.

In the region of the microsparger, the upper part comprises segment-shaped openings towards the aeration channel, the aeration channel being covered or sealed by an annular aeration ring made from the porous material forming the gas outlet openings. It is, however, also possible in principle to insert the aeration ring directly into the upper part.

The upper part may be sealed relative to the lower part comparatively simply by seals, for example O-ring cord seals or O-rings.

In further preferred embodiments, the upper part may be either welded or adhesively bonded to the lower part.

According to a further preferred embodiment of the invention, the inflows for independent supply of the aeration channels in each case comprise a tube connection with a nonreturn valve. The nonreturn valves reliably prevent backflow of media from the reactor interior into the aeration device.

According to a further preferred embodiment of the invention, the housing comprises a central opening adjusted to a stirrer flange of the bioreactor and may be arranged upstream of a stirrer on the bottom of an interior of the bioreactor. Thanks to the central opening of the aeration device, the latter may be positioned optimally relative to a stirrer arranged in the reactor interior. The volumetric flow rates of the aeration elements may be adapted to the reactor volume by being differently dimensioned. In particular in the case of the ring sparger, the number of holes may be adjusted to the volume or effective volume of the reactor. For example, one hole may be arranged in the ring sparger for each 10 liters of effective volume. In the case of the microsparger, its surface area is likewise adapted to the reactor volume, for example 2 to 2.5 cm2 per 10 liters of effective volume. In this manner, a constant bubble size distribution may be achieved combined with any desired scalability of the reactor volume.

In addition to the number of gas outlet openings or holes, the size thereof may also be adapted to the desired volumetric flow rates. In the case of microspargers, the porosity and the surface area thereof may be correspondingly adapted.

According to another preferred embodiment of the invention, the lower part comprises a continuous, circular bottom and may be inserted in sealing manner into the bottom of the bioreactor by a screw, bayonet, latch, clamp, adhesive or clip connection.

Further details of the invention may be inferred from the following detailed description and the attached drawings, which illustrate preferred embodiments of the invention by way of example.

BRIEF DESCRIPTION OF THE DRAWINGS

FIG. 2 is a side view of the aeration device of FIG. 1 suction sectioned along line II-II.

FIG. 3 is a side view of the aeration device of FIG. 1 sectioned along line III-III.

DETAILED DESCRIPTION OF THE PREFERRED EMBODIMENTS

Figure 1:
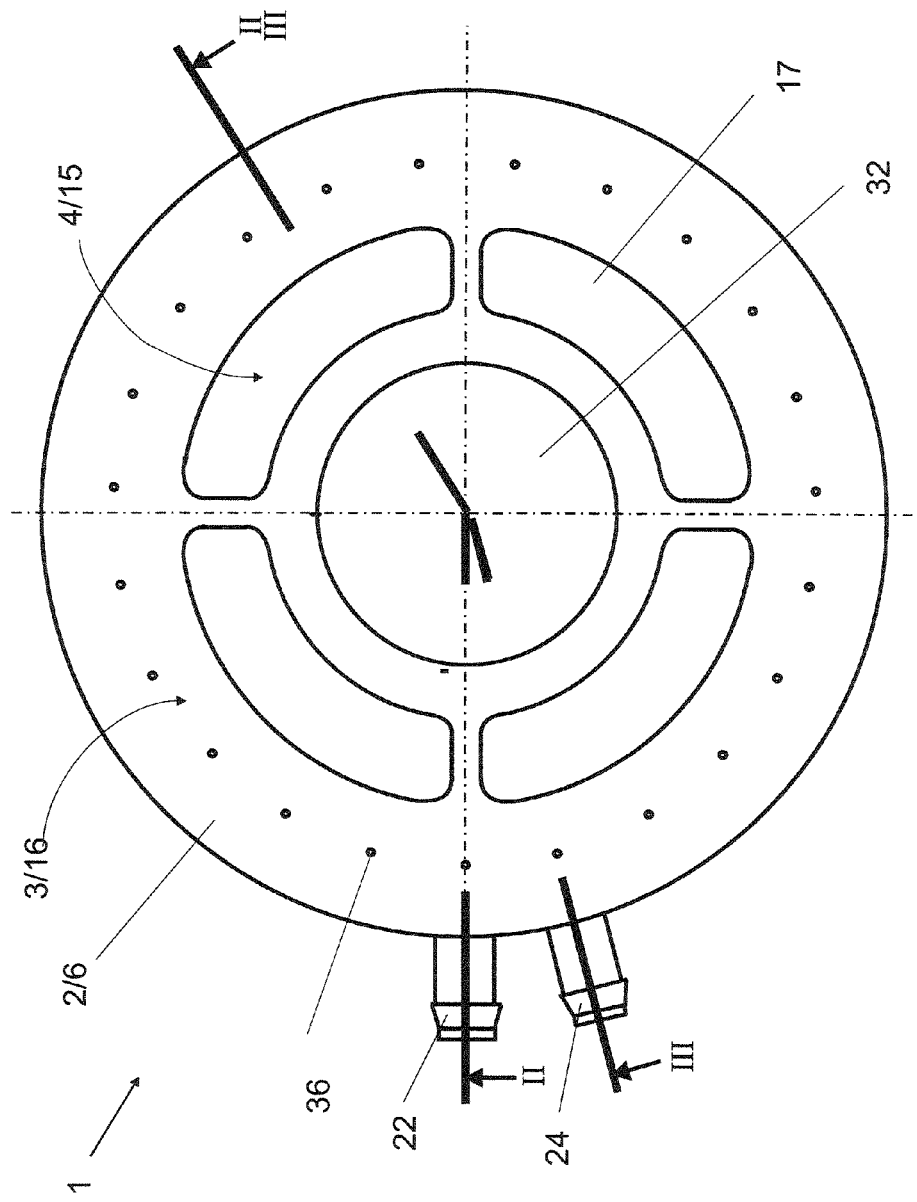
FIG. 1 is an enlarged plan view of a medium-sized aeration device.

An aeration device 1 substantially consists of a housing 2 with a first aeration element 3 and a second aeration element 4.

The housing 2 consists of a lower part 5 and an upper part 6 positionable on the lower part 5. The lower part 5 comprises two aeration channels 7, 8 arranged concentrically to one another. The aeration channels 7, 8 are downwardly delimited in the vertical direction by a bottom 9 of the lower part 5. The first aeration channel 7 is laterally delimited by the outer wall 10 and, towards the second aeration channel 8, by a partition wall 11. The second aeration channel 8 is correspondingly delimited towards the first aeration channel 7 by the partition wall 11 and, on the side thereof remote from the first aeration channel 7, by an inner wall 12 of the lower part 5.

The second aeration channel 8 comprises on the side thereof remote from the bottom 9 an annular step 13, into which may be inserted an annular aeration ring 14, which closes off the second aeration channel 8 upwardly in a vertical direction. The aeration ring 14 consists of a sintered porous material which forms the gas outlet openings of the second aeration element 4, which takes the form of a "microsparger" 15. The aeration ring 14 correspondingly comprises gas outlet openings, the diameter of which is less than 0.1 mm.

The upper part 6 positionable on the lower part 5 closes the first aeration channel 7 and forms with the latter the first aeration element 3. To this end, the upper part 6 comprises gas outlet openings 36 in the region of the aeration channel 7, the diameter of which openings is greater than 0.1 mm. The first aeration element 3 consequently forms a "ring sparger" 16.

In the region of the second aeration channel 8, the upper part 6 comprises segment-shaped openings 17, which leave the aeration ring 14 exposed in the substantial regions thereof comprising the gas outlet openings 36.

Sealing between the lower part 5 and upper part 6 is provided by in each case arranging seals 18, 19, 20, which take the form of O-ring cord seals or O-rings, on the walls 10, 11, 12.

The first aeration channel 7 comprises a radially extending first inflow 21 which leads into a tube connection 22. The second aeration channel 8 correspondingly comprises a second radially extending inflow 23 which leads into a tube connection 24. Nonreturn valves (not shown) may be arranged in the tube connections 22, 24 or in the inflows 21, 23.

Figure 4:
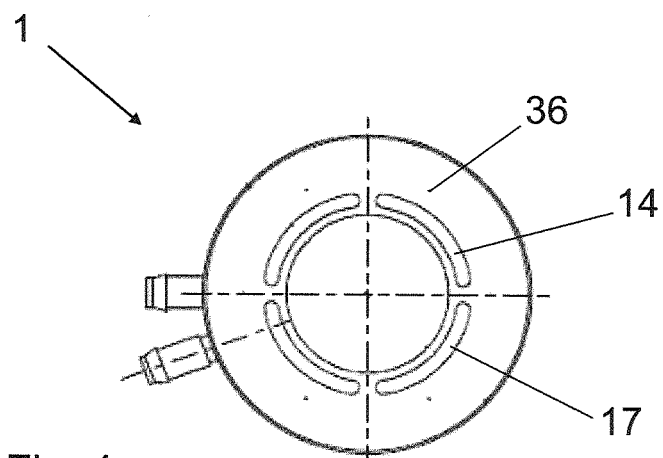
FIG. 4 is a plan view of a further aeration device of a smaller size than the aeration device of FIG. 1.
Figure 5:
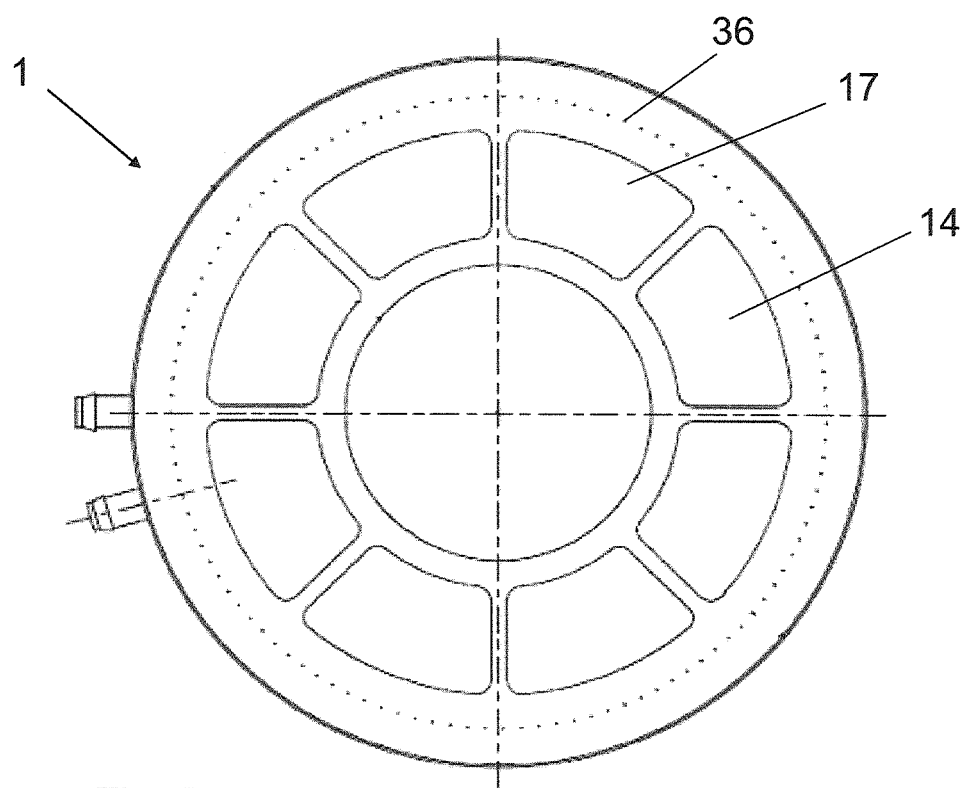
FIG. 5 is a plan view of a further aeration device of a larger size than the aeration device of FIG. 1.

FIGS. 4 and 5 show two further exemplary embodiments of the aeration device which enable any desired scalability of the aeration device for transition from a smaller to a larger effective reactor volume. Said scalability is achieved on the one hand by varying the number of gas outlet openings 36 in the ring sparger 3 and on the other hand by the number and area of the segment-shaped openings 17 of the aeration ring 14, in which the porous, gas-permeable material is located. The aeration ring 14 preferably comprises one gas passage opening 36 per 10 liters of effective reactor volume, while the area of the segment-shaped openings 17 comprising porous material preferably amounts to 2 to 2.5 cm2 per 10 liters of effective reactor volume.

Figure 6:
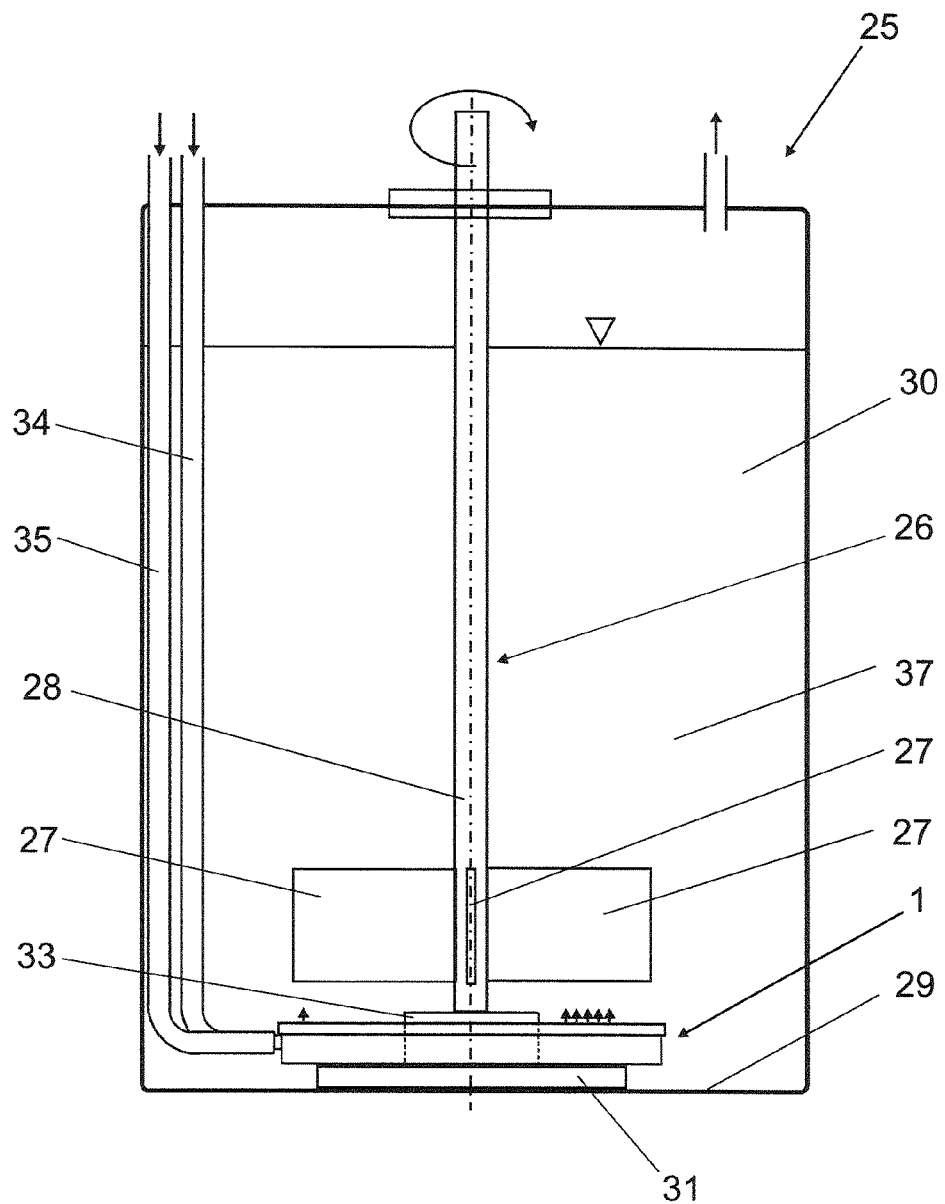
FIG. 6 is a side view of a bioreactor with stirrer and an aeration device.

FIG. 6 shows by way of example a bioreactor 25, which for example takes the form of a flexible pouch for single use and comprises a stirrer 26, which may be driven from outside, with stirrer blades 27. The bioreactor 25 comprises an interior 30, on the bottom 29 of which is arranged a stirrer flange 31. The stirrer shaft 28 is mounted rotatably in the stirrer flange. The aeration device 1 is pushed with its central opening 32 onto a shoulder 33 of the stirrer flange 31. Gas is supplied via a first inflow line 34 to the first inflow 21 and via a second inflow line 35 to the second inflow 23, which gas emerges from the aeration device 1 and forms bubbles in the liquid medium 37 in the interior 30.

Further inflows and outflows and open- and closed-loop control devices are not shown.

In a preferred embodiment, the dimensioning ratio between the diameter of the aeration device 1 and the diameter of the bioreactor 25 preferably amounts to between 0.1 and 0.5, particularly preferably to 0.240. The dimensioning ratio between the aeration device 1 and the diameter of the stirrer blades 27 amounts to between 0.4 and 0.7, preferably to 0.622.

In one preferred design of the aeration device, the upper and lower part of the aeration device is manufactured from a plastics material sterilizable with gamma radiation, preferably polycarbonate, while the porous material in the segment-shaped openings 17 consists of polyethene.

Figure 7:
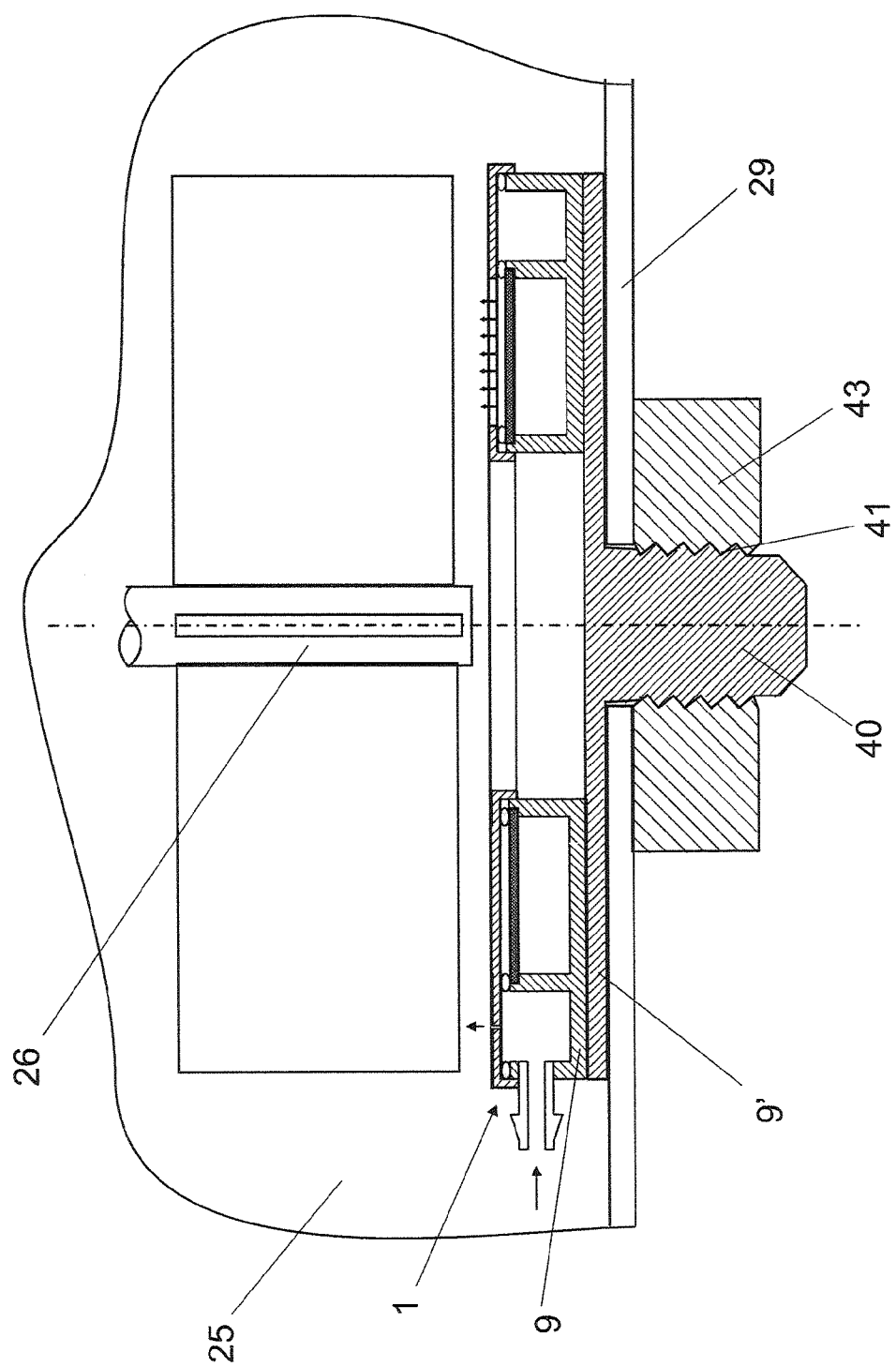
FIG. 7 is a side view of a further bioreactor with an aeration device, the lower part of which, by means of a continuous bottom, may be inserted by a screw connection into the bottom of the bioreactor.
Figure 8:
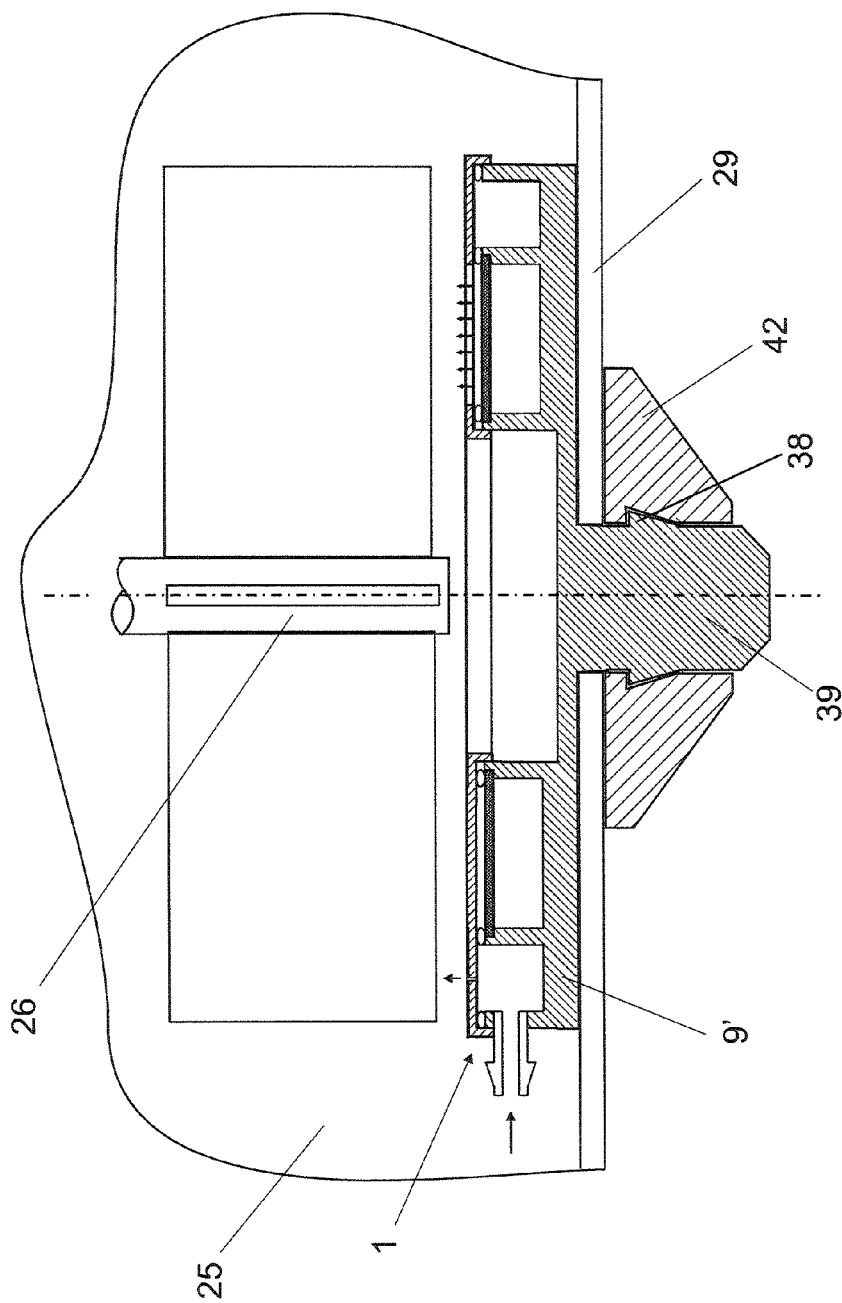
FIG. 8 is a side view of a further bioreactor with an aeration device, the lower part of which, by means of a continuous bottom, may be inserted by a latch connection into the bottom of the bioreactor.

In further embodiments according to FIGS. 7 and 8, the aeration device 1 may be fastened, optionally using sealing elements, via a screw, bayonet, latch, clamp, adhesive or clip connection on the lower part 5 of the aeration device 1 in a circular opening in the lower part of the bioreactor 25 and optionally replaced after use. In these embodiments, the lower part 5 comprises a continuous, circular bottom (9'). The bottom 9' may be firmly connected to the bottom 9 or, instead of the annular bottom 9 shown in FIGS. 2 and 3, may form the bottom of the lower part 5. For the purpose of inserting the aeration direction into the lower part of the bioreactor, it is advantageous for at least part of the bottom 29 of the bioreactor 25 around the circular opening to be manufactured from a rigid material. The aeration device 1 is fastened in fluid-tight manner in the bioreactor bottom 29 by latching via the peripheral latching lug 38 or screwing via the thread 41 of the central piece 39, 40 of the aeration device 1 with the clamping part 41, 42. This embodiment permits flexible insertion and replacement of the aeration device in both single- and multiple-use bioreactors.

The invention claimed is:

1. An aeration device (1) for a bioreactor (25), comprising: a housing (2) formed separate from the bioreactor (25) and having:
   a lower part (5) with an annular bottom wall (9), first, second and third substantially concentric annular walls (10, 11, 12) projecting up from the bottom wall (9) to define a first aeration channel (7) between the first and second annular walls (10, 11) and a second aeration channel (8) between the second and third annular walls (11, 12);
   an aeration member (14) supported on ends of the second and third annular walls (11, 12) remote from the bottom wall (9) and covering the second aeration channel (8) to form a second aeration element (4), the aeration member (14) having a lower surface facing into the second aeration channel (8) and an upper surface facing away from the second aeration channel (8), the aeration member (14) being formed from a porous material with second gas outlet openings of a second size extending from the lower surface to the upper surface; and
   an upper part (6) having a first circumferential wall supported on the first and second annular walls of the lower part (5) and facing into the first aeration channel (7), the upper part further having a second circumferential wall supported on the third annular wall (12) of the lower part (5), circumferentially spaced bridges extending between the first and second circumferential walls of the upper part (6) and facing the upper surface of the aeration member (14), segment shaped openings (17) being defined circumferentially between the bridges of the upper part (6) and radially between the first and second annular walls so that the upper surface of the aeration member (14) is exposed to areas external of the aeration device (1), the first circumferential wall of the upper part (6) being formed with first gas outlet openings (36) of a first size that differs from the second size, the first circumferential wall of the upper part (6) and the first aeration channel (7) of the lower part (5) defining a first aeration element (43).

2. The aeration device of claim 1, wherein the housing (2) is an annular disk in which are arranged the first and second aeration elements (3, 4).

3. The aeration device of claim 1, wherein the first aeration element (3) is a ring sparger (16) with the first gas outlet openings (36) being greater than 0.1 mm in diameter and the second aeration element (4) is a microsparger (15) with the second gas outlet openings (36) being less than 0.1 mm in diameter.

4. The aeration device of claim 3, wherein the gas outlet openings of the microsparger (15) are formed by a sintered porous material.

5. The aeration device of claim 1, wherein the first aeration element (3) is a ring sparger with the first gas outlet openings of the first size and the second aeration element (4) is a ring sparger (16) with the second gas outlet openings (36) of the second size, the first and second gas outlet openings (36) being larger than 0.1 mm.

6. The aeration device of claim 1, wherein the first aeration element (3) is a microsparger with the first gas outlet openings of the first size and the second aeration element (4) is a microsparger (15) with the second gas outlet openings (36) of the second size, the first and second gas outlet openings (36) being smaller than 0.1 mm.

7. The aeration device of claim 1, wherein the lower part (5) of the housing (2) further has first and second radially extending inflows (21, 23) communicating respectively with the first and second aeration channels (7, 8).

8. The aeration device of claim 7, wherein the first and second inflows (21, 23) are provided respectively with first and second tube connections (22, 24) each of which has a nonreturn valve for independent supply of the aeration channels (7, 8).

9. The aeration device of claim 1, wherein the upper part (6) is sealed relative to the lower part (5) by seals (18, 19 20).

10. The aeration device of claim 1, wherein the upper part (6) is welded to the lower part (5).

11. The aeration device of claim 1, wherein the upper part (6) is adhesively bonded to the lower part (5).

12. The aeration device of claim 1, wherein the housing (2) comprises a central opening (32) dimensioned to accommodate a stirrer flange (31) of the bioreactor (25) and is arranged between a stirrer (26) and a bottom (29) of an interior (30) of the bioreactor (25).

13. The aeration device of claim 7, wherein the lower part (5) comprises a continuous, circular bottom wall (9') and is inserted in sealing manner into a bottom (29) of the bioreactor (25) by a screw, bayonet, latch, clamp, adhesive or clip connection.

14. The aeration device of claim 1, wherein the upper part (6) has between 4 and 8 of the segment shaped openings (17).

15. The aeration device of claim 1, wherein the bridges of the upper part (6) are radially extending bridges extending between inner and outer circumferential areas of the upper part (6) and separating the segment shaped openings (17), each of the segment shaped openings (17) being circumferentially larger than each of the radially extending bridges.

\* \* \* \* \*